(12) United States Patent
Gessler et al.

(10) Patent No.: US 12,144,958 B2
(45) Date of Patent: Nov. 19, 2024

(54) DRIP CHAMBER WITH AUTOMATIC VENT AND SHUTOFF

(71) Applicant: Mobile I.V. Systems, LLC, Chugiak, AK (US)

(72) Inventors: Ryan Gessler, Chugiak, AK (US); Dale Constuble, Chugiak, AK (US); Richard Stryken, Chugiak, AK (US); Gerold Gugle, Chugiak, AK (US)

(73) Assignee: Mobile I.V. Systems, LLC, Chugiak, AK (US)

( * ) Notice: Subject to any disclaimer, the term of this patent is extended or adjusted under 35 U.S.C. 154(b) by 0 days.

(21) Appl. No.: 18/253,027

(22) PCT Filed: Oct. 4, 2021

(86) PCT No.: PCT/US2021/053410
§ 371 (c)(1),
(2) Date: May 15, 2023

(87) PCT Pub. No.: WO2022/076325
PCT Pub. Date: Apr. 14, 2022

(65) Prior Publication Data
US 2024/0050643 A1 Feb. 15, 2024

Related U.S. Application Data

(60) Provisional application No. 63/087,778, filed on Oct. 5, 2020.

(51) Int. Cl.
*A61M 5/14* (2006.01)
*A61M 5/38* (2006.01)

(52) U.S. Cl.
CPC ............ *A61M 5/1411* (2013.01); *A61M 5/38* (2013.01)

(58) Field of Classification Search
CPC .............. A61M 5/1411; A61M 1/3627; A61M 5/16822; A61M 5/1689; A61M 5/38;
(Continued)

(56) References Cited

U.S. PATENT DOCUMENTS 3,776,229 A * 12/1973 McPhee ................ A61M 5/1411
604/254
3,854,907 A * 12/1974 Rising ................. B01D 19/0031
604/407

(Continued)

FOREIGN PATENT DOCUMENTS

CN 104491949 * 4/2015
CN 104491949 A 4/2015
(Continued)

OTHER PUBLICATIONS

International Search Report and Written Opinion received in PCT Application No. PCT/US2021/053410 dated Jan. 27, 2022.
(Continued)

*Primary Examiner* — Theodore J Stigell
(74) *Attorney, Agent, or Firm* — Dorsey & Whitney LLP

(57) ABSTRACT

An apparatus for automatically setting and maintaining a fluid level in a drip chamber is described. A drip chamber according to one embodiment includes a drip chamber body defining an internal volume, an inlet tube configured for dripping fluid into the interior of the drip chamber, an outlet tube in fluid communication with the interior of the drip chamber, and an air vent configured to automatically prevent the venting of air out of the interior of the drip chamber if the fluid filling the interior of the drip chamber is above a predetermined fill level, and to automatically vent air out of the drip chamber when the fluid falls below the predetermined fill level, the predetermined fill level corresponding to a volume less than the internal volume of the drip chamber.

19 Claims, 7 Drawing Sheets

(58) Field of Classification Search
CPC .......... A61M 5/40; A61M 5/385; A61M 5/36; A61M 2039/205
See application file for complete search history.

(56) References Cited

U.S. PATENT DOCUMENTS

| | | | | |
|---|---|---|---|---|
| 4,013,072 | A * | 3/1977 | Jess | A61M 5/165 |
| | | | | 137/197 |
| 5,242,424 | A * | 9/1993 | Chen | A61M 5/1411 |
| | | | | 604/122 |
| 5,779,674 | A * | 7/1998 | Ford | A61M 5/38 |
| | | | | 604/122 |
| 9,533,109 | B2 | 1/2017 | Bryan | |
| 2002/0029021 | A1 * | 3/2002 | Bormann | A61M 5/1411 |
| | | | | 604/252 |
| 2003/0040707 | A1 | 2/2003 | Kappel et al. | |
| 2011/0275988 | A1 | 11/2011 | Davis et al. | |

FOREIGN PATENT DOCUMENTS

| | | |
|---|---|---|
| WO | 2015188576 A1 | 12/2015 |
| WO | 2021021756 A1 | 2/2021 |
| WO | 2022076325 | 4/2022 |

OTHER PUBLICATIONS

PCT Application PCT/US21/53410 titled "Drip Chamber With Automatic Vent and Shutoff" filed Oct. 4, 2021.
U.S. Appl. No. 63/087,778 titled "Drip Chamber With Automatic Vent and Shutoff" filed Oct. 5, 2020.

* cited by examiner

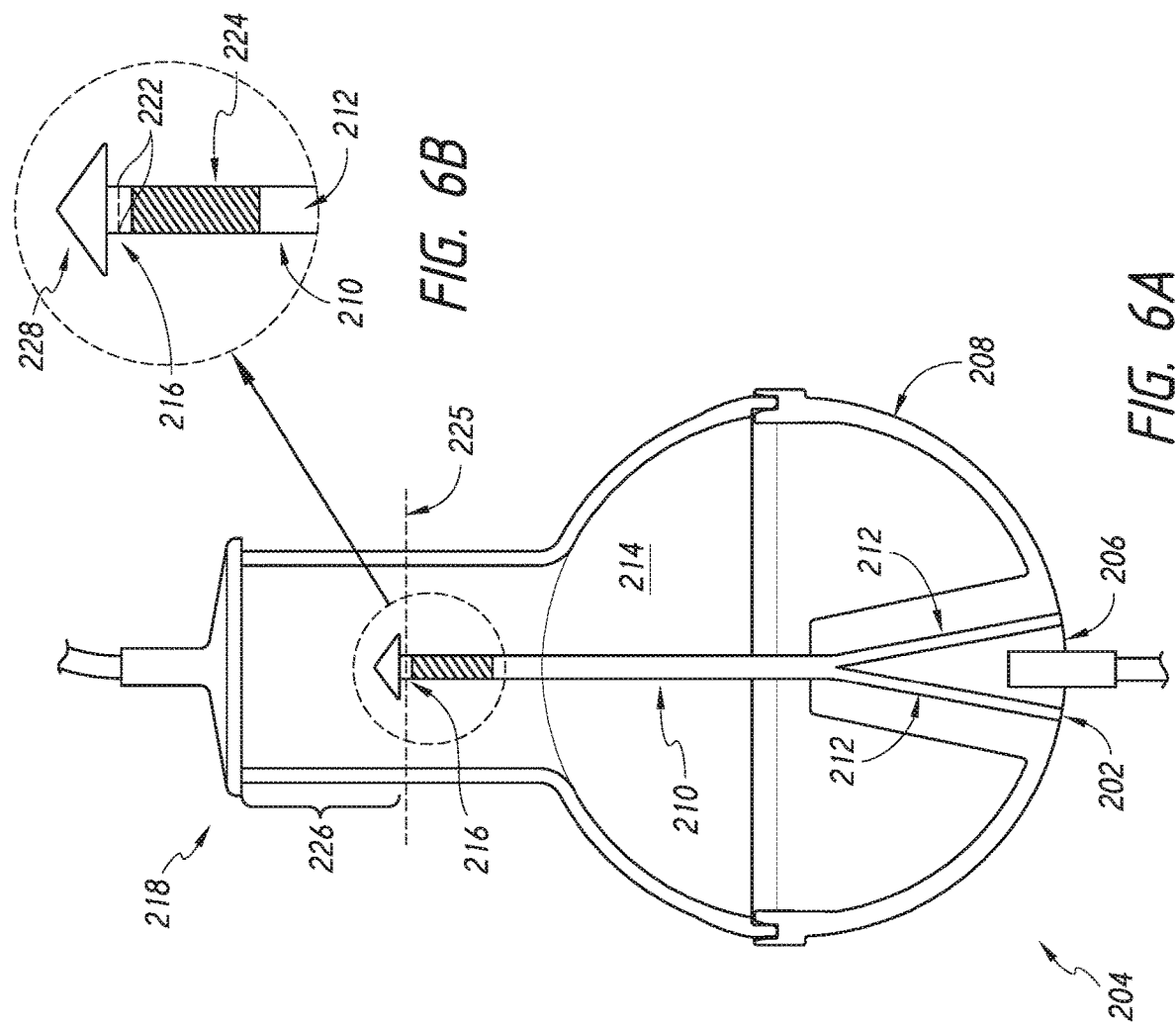

DRIP CHAMBER WITH AUTOMATIC VENT AND SHUTOFF

CROSS-REFERENCE TO RELATED APPLICATIONS

This application is a 35 U.S.C. § 371 National Stage Application of International Application No. PCT/US2021/053410, filed 4 Oct. 2021, entitled "DRIP CHAMBER WITH AUTOMATIC VENT AND SHUTOFF", which claims priority to U.S. Provisional Application No. 63/087,778 filed Oct. 5, 2020, entitled "DRIP CHAMBER WITH AUTOMATIC VENT AND SHUTOFF", which are incorporated herein by reference, in their entirety, for any purpose.

TECHNICAL FIELD

This application describes an automatic vent with shutoff for establishing and maintaining the size of the air pocket within a drip chamber for intravenous (IV) fluid infusion.

BACKGROUND

IV therapy refers to the delivery of a liquid substance (e.g., a glucose solution, saline solutions, medication in liquid form, an aqueous physiologically-acceptable fluid, and blood or plasma) directly into a vein. One method of administering IV fluids is through gravity assisted infusion and is commonly referred to as an IV drip. Sometimes, IV fluids may be administered with the assistance of a pressurized cuff designed to maintain the rate of IV fluid delivery to the patient. While IV therapy has been widely available since the mid-1900s, commercially available IV infusion sets have remained mostly unchanged for decades and many risks and inefficiencies associated with them remain largely unaddressed. For example, a significant risk associated with IV therapy is air embolism, which can result from air passing through the fluid line into the circulatory system of the patient and causing a blood vessel blockage. To reduce the risk of this, the IV bag is typically held at least 3 feet above the IV site and the drip chamber is held vertical at all times, which may be difficult to achieve in certain scenarios, such as in emergency response scenarios. Priming the IV tube set through conventional means may also have shortcomings largely unaddressed by IV tube sets currently in wide use. Thus, designers and manufacturers of IV tube sets continue to seek improvements thereto and embodiments described herein may address some of the limitations of existing solutions.

SUMMARY

An apparatus for automatically setting a fluid level and maintaining the fluid level setting in a drip chamber is described. The apparatus may be incorporated in a drip chamber for intravenous (IV) fluid infusion, which may optionally be an all position drip chamber (also referred to herein as an emboli-reducing drip chamber), thereby further reducing the risk of embolism. A drip chamber according to some embodiments of the present disclosure includes a drip chamber body defining an internal volume within an interior of the drip chamber body, an inlet tube configured to drip the IV fluid into the interior of the drip chamber, an outlet tube in fluid communication with the interior of the drip chamber body to allow the IV fluid to flow out of the drip chamber body, and a vent configured to automatically set and maintain an air pocket of predetermined size within the interior of the drip chamber. In some embodiments, the vent includes a vent opening coupling the interior of the drip chamber to ambient air, and a pickup tube having a first end in fluid communication with the vent opening and a second end comprising an intake opening at a location spaced apart from the vent opening to define the predetermined size of the air pocket. The location of the intake opening is predetermined (or fixed) and does not change during operation/use of the drip chamber, thus allowing the intake opening to define an air pocket of a predetermined size within the interior volume of the drip chamber.

In some embodiments, the vent comprises an aquaphobic filter operatively coupled to the second end of the pickup tube near the intake opening, the aquaphobic filter configured to substantially prevent the IV fluid from passing therethrough.

In some embodiments, the pickup tube extends into the interior of the drip chamber to a location located distally from an internal opening of the outlet tube.

In some embodiments, the drip chamber also includes a cap that includes the inlet tube, wherein the vent opening is formed in the cap, and wherein the pickup tube extends proximally from the cap.

In some embodiments, the pickup tube is integrated into a wall of the drip chamber, with a lengthwise direction of the pickup tube extending along the wall of the drip chamber.

In some embodiments, the pickup tube is spaced apart from a wall of the drip chamber.

In some embodiments, the pickup tube is fixed to an annular base having a central aperture, the annular base operatively coupled to an underside of the cap such that the inlet tube passes through the central aperture of the annular base.

In some embodiments, the vent opening is located on a proximal side of the drip chamber and wherein the pickup tube extends distally into the drip chamber.

In some embodiments, the intake opening is substantially axially aligned with the distal opening of the outlet tube.

In some embodiments, the pickup tube is one of a plurality of pickup tubes of a vent cage positioned above and co-axially aligned with the outlet tube, each of the plurality of pickup tubes arranged radially around a periphery of the vent cage.

In some embodiments, the vent opening is provided by a plurality of discrete through-holes in a proximal wall of the drip chamber, the plurality of discrete through-holes corresponding in number to the plurality of pickup tubes. In some such embodiments, the vent cage includes a base configured to provide each of the plurality of pickup tubes in fluid communication with a corresponding one of the plurality of discrete through-holes. In some embodiments, the vent cage further includes, a roof that defines a central blind hole substantially coaxial with and facing the outlet tube, wherein the intake opening of each of the plurality of pickup tubes is in fluid communication with central blind hole. In some embodiments, the vent cage further includes an aquaphobic filter across the central blind hole such that a fluid path from the interior of the drip chamber to each of the pickup tubes passes through the aquaphobic filter.

A drip chamber for intravenous (IV) fluid infusion according to further embodiments of the present disclosure includes a drip chamber body defining an internal volume within an interior of the drip chamber, an inlet tube configured to drip the IV fluid into the interior of the drip chamber, an outlet tube in fluid communication with the interior of the drip chamber to allow the IV fluid to flow out of the drip chamber, and an air vent configured to automatically close and prevent venting of gases out of the interior of the drip chamber if the IV fluid filling the interior of the drip chamber is above a predetermined fill level, and to automatically vent gasses out of the drip chamber when the IV fluid falls below the predetermined fill level, the predetermined fill level corresponding to a volume less than the internal volume of the drip chamber.

BRIEF DESCRIPTION OF THE DRAWINGS

The accompanying drawings, which are incorporated in and constitute a part of the specification, illustrate examples of the disclosure and, together with the general description given above and the detailed description given below, serve to explain the principles of these examples.

FIGS. 6A and 6B shows a simplified illustration and a detail thereof, respectively, of a drip chamber with an auto vent-shutoff feature that vents at a proximal end of the drip chamber according to some examples herein.

DETAILED DESCRIPTION

Figure 1:
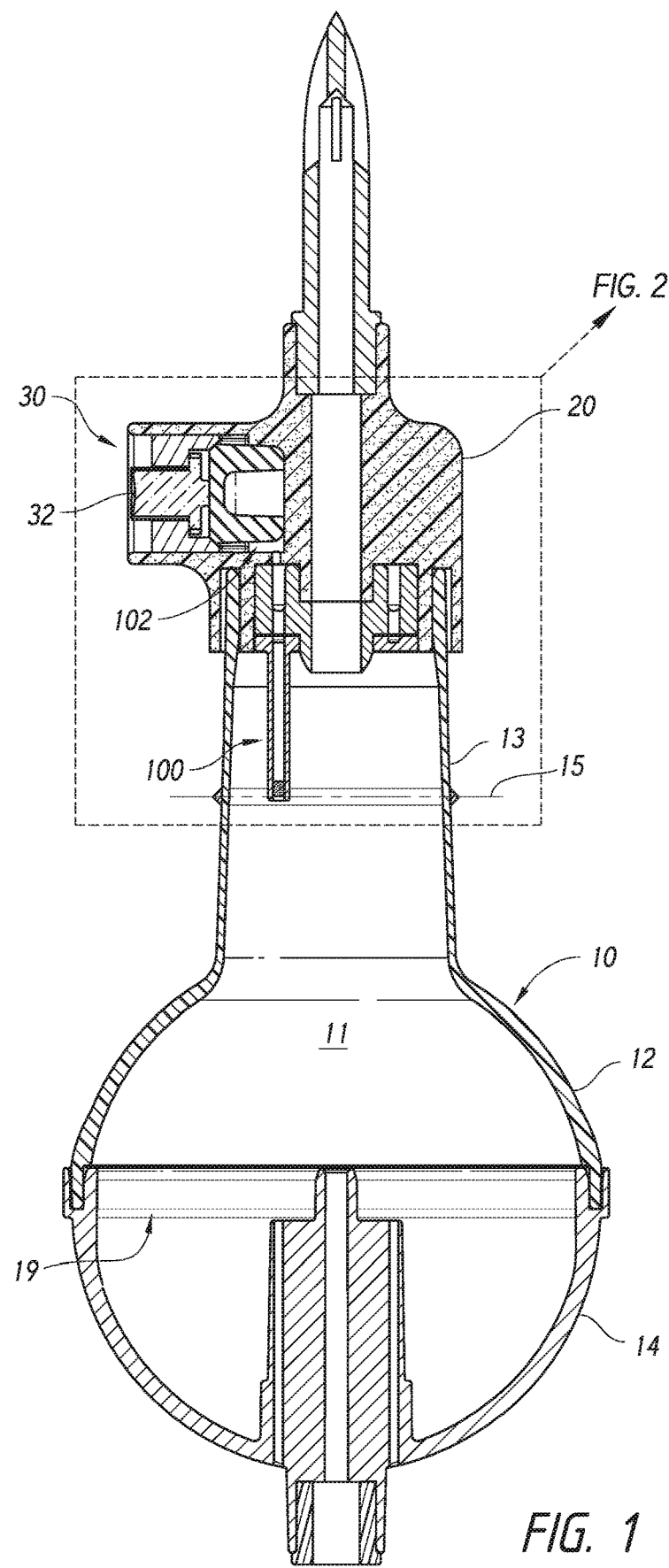
FIG. 1 shows a cross-sectional view of an emboli-reducing drip chamber with a spike cap and an auto vent-shutoff feature according to the present disclosure.

Generally, the embodiments described herein relate to IV infusion systems, and more particularly to IV tube sets and apparatuses associated with the same. In typical embodiments, a fluid infusion set (e.g., an IV tube set) includes a drip chamber, which may be, but need not be, an emboli-reducing drip chamber (also referred to as all position drip chamber). Examples of an all position drip chamber are described in U.S. Pat. No. 10,485,921, entitled "Drip chamber assembly that functions irrespective of orientation," which is incorporated herein by reference in its entirety for any purpose.

A drip chamber is connected in the fluid path between the IV bag and the IV site in the patient, and serves the primary function of enabling a user (e.g., the clinician or person administering the IV fluid) to confirm the drip rate, such as by counting the number of drops per minute. The drip chamber is configured to be connected to an IV bag. For example, in some cases, the cap of the drip chamber has a spike integrated in the cap for connecting the drip chamber directly to the IV bag. In other instances the spike may be located at the end of tubing that extends from a distal end of the drip chamber. As used herein, the terms proximal and proximally are used to describe a positions or direction closer to the patient during use, while the terms distal and distally refer to the relative position or direction which is relatively farther from the patient during use. While IV fluid is being administered, the fluid flows from the bag into the drip chamber and toward the IV site in the patient, thus the distal and proximal direction or position may also be described as upstream and downstream, respectively, in reference to the direction of fluid flow. For confirming the drip rate, an inlet tube providing the IV fluid into the drip chamber is configured to drip the fluid into the drip chamber. The team configured to drip implies that the proximal diameter of the inlet tube is sufficiently small such that the liquid flows into the drip chamber at a drip rate rather than as a continuous stream. The drip chamber is further configured, such that during use, air pocket remains in its upper portion, above the fluid, to enable the drops to be seen and counted.

A sealed IV bag typically contains a certain amount of gas, typically air, sealed with the fluid in the bag. This air, or a portion thereof, may and often is transferred to the drip chamber during priming of the drip chamber and administration of fluid. While a certain amount of air is useful in the drip chamber to establish/maintain an air pocket for counting the drops, as described above, too much air in the drip chamber increases the risk of air embolism. As such, solutions have been introduced for substantially purging the air out of the IV bag and thus reducing and/or control the amount of air that can be introduced into the drip chamber. As an example, PCT/US2020/043776, entitled "Priming Apparatus For A Drip Chamber of A Fluid infusion System," the entirety of which is incorporated herein by reference for any purpose, describes a priming apparatus that enables substantially all of the excess air to be purged from the upstream system and then to selectively and reversibly seal the upstream fluid system, preventing the introducing from any additional air therein until the IV bag is exhausted and needs to be replaced. This priming apparatus also facilitates a more rapid priming of the drip chamber. The increased speed with which the drip chamber is primed (i.e. initially partially filled with IV fluid) with a priming apparatus such as the one described in PCT/US2020/043776, may increase the risk of overfilling the drip chamber, for example if the priming valve is held open for too long, which may shrink or eliminating the drip-counting air pocket in the drip chamber making it more difficult or impossible to confirm the drip rate. A drip chamber with a self-regulating air pocket is described herein. Embodiments of the present disclosure automatically establish an air pocket within the drip chamber and protect the size of the air pocket during fluid administration, e.g., using an automatic vent shut-off assembly according to the present disclosure. Apparatuses for automatically setting and maintaining a fluid level in a drip chamber are described.

Figure 2:
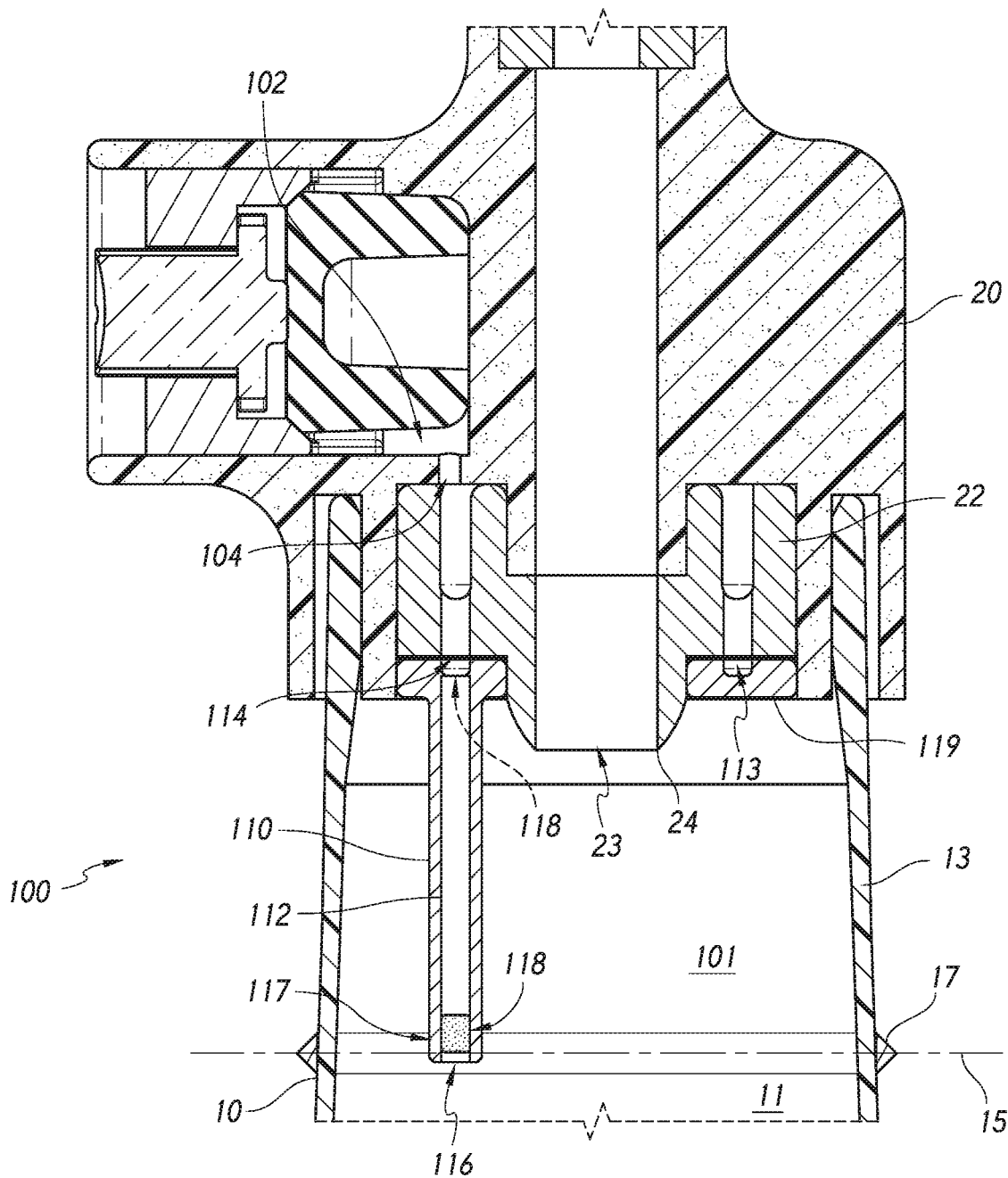
FIG. 2 shows an enlarged view of a portion of the drip chamber assembly in FIG. 1.

FIGS. 1 and 2 show an embodiment of an automatic vent shut and off assembly 100, also referred to as autovent assembly, shown as part of a drip chamber 10 equipped with a priming apparatus 30. The priming apparatus 30 (e.g., valve 32) may be implemented according to any of the examples in PCT/US2020/043776. In other embodiments, a different priming mechanism may be used. In some embodiments, the drip chamber 10 may not include a priming apparatus but may instead be configured for priming via conventional means (e.g., by squeezing or pumping the drip chamber or portion thereof). Also, while FIG. 1 depicts an example in which the drip chamber 10 is an emboli-reducing drip chamber, an autovent assembly, such as autovent assembly 100, may be included in a conventional drip chamber designed to be held vertically during use. It will be understood that autovent assemblies according to any of the examples herein can be used with a drip chamber of any configuration or design. In the embodiment shown in FIGS. 1 and 2, the autovent assembly 100 includes a vent 102 having a vent opening 104, in this case provided in the cap 20 of the drip chamber 10. The vent 102 is configured to vent air out of the drip chamber 10 while filling the drip chamber 10 with IV fluid. The vent 102 is configured such that the flow of air out of the vent 102 automatically stops when the drip chamber 10 is filled to a predetermined fill level 15. In this example, the vent 102 is provided in the upper portion of the drip chamber assembly, specifically in the cap 20 which extends across the distal side of the drip chamber 10, covering the inlet of neck portion 13. In some embodiments, a visual indicator 17 of the fill level 15 (e.g., a fill line) is provided, for example on the neck portion 13 if the drip chamber 10.

A vent pickup tube 110 extends from the vent opening 104 toward the interior of the drip chamber 10. In this example, the vent pickup tube 110 is coupled to the underside of cap 20 and extends, from the distal end of the drip chamber 10 generally proximally or in the downstream direction. In other embodiments, the vent opening may be located elsewhere on the drip chamber and a vent pickup tube may thus be configured differently (e.g., to extend generally upstream), e.g., as described further below. The vent pickup tube 110 defines a passage 112 that connects a first, in this case its distal, opening 114 of the pickup tube 110 to a second, in this case its proximal, opening 116. The first opening 114 is located proximate the vent opening 104 and the second opening 116 is spaced apart therefrom and is located within the interior of the drip chamber 10, that is, within the internal volume 11 define by drip chamber 10. The vent pickup tube 110 relocates the air vent intake to a location within the interior volume 11, spaced away from the outer walls or other structure(s) that define the interior volume of the drip chamber. A fluid stop or plug 118 is operatively associated with the vent pickup tube 110. The plug 118, in cooperation with the diameter of passage 112, resists or substantially blocks the passage of a fluid through the pickup tube 110 while permitting the passage of air therethrough. The plug 118 may be made from a filter material, which may be hydrophobic (or aquaphobic) in some embodiments. In some embodiments, the permeability (or porosity) of the filter material is selected to allow gases to pass through but not water. In some embodiments, the filter material selected for the plug 118 is additionally or alternatively, aquaphobic, thereby allowing air to pass through while resisting or substantially blocking the IV fluid (typically an aqueous solution) from passing through it. In cases in which the drip chamber is designed for use with non-aqueous IV solution, a different type of filter of suitable configuration to resist or effectively block the passage of the non-aqueous fluid through the vent may be used.

In some embodiments, the plug 118 is located near the first opening 114. In other embodiments, the plug 118 may be located at the second or terminal end 117 of the pickup tube 110, proximate to the second opening 116. The plug 118 may be located anywhere along the length of the passage 112. In some embodiments, any portion of the length, in some cases substantially the full length, of passage 112 may be filled with the aquaphobic filter material of plug 118 to provide sufficient resistance to the passage of a liquid therethrough, while still permitting air to be vented out of the drip chamber. The vent pickup tube 110 is configured to position the second (internal) opening 116 at the desired fill level 15. For example, if the opening 116 is at the terminal end 117 of the pickup tube 110 as is the case in the present example, the length of the pickup tube 110 establishes the desired size (e.g., the height) of the air pocket 101. The air pocket 101 is then automatically maintained by the autovent assembly 100 (e.g., by the pickup tube 110 and aquaphobic plug 118). The diameter of the passage 112 is substantially small to create sufficient surface tension and resistance to the outflow of liquid out the drip chamber, which works in cooperation with the aquaphobic plug 118 for effectively reject fluid from passing through the vent 102. As such an air pocket 101 is defined and automatically maintained above fill level 115 by the autovent assembly 100 (e.g., by pickup tube 110). In this manner, the autovent assembly 100 automatically sets the fill level 115 to the predetermined vertical location of the opening 116.

In some embodiments, the vent pickup tube 110 may be manufactured separately from the drip chamber 10 and/or cap 20 and operatively assembled for use as shown in FIGS. 1 and 2. for example, the vent pickup tube 110 may be provided with a base 119 in the shape of a ring and which is positioned around the tubular projection 24 of a cap filter assembly 22. The pickup tube 110 may be substantially axially aligned with the vent opening 104 as shown in the example in FIGS. 1 and 2. In other examples, the vent pickup tube 110 may be located at a different radial location of the ring base 119 and an annular passage 113 in the ring base 119 may communicate the air from the passage 112 of the pickup tube 110 to the vent opening 104. Also, the internal opening 116 may be located elsewhere along the length of the tube 110, other than the terminal end 117, as long as the fluid path from the interior of the drip chamber and out the vent 102 passes through the plug 118.

Figure 3:
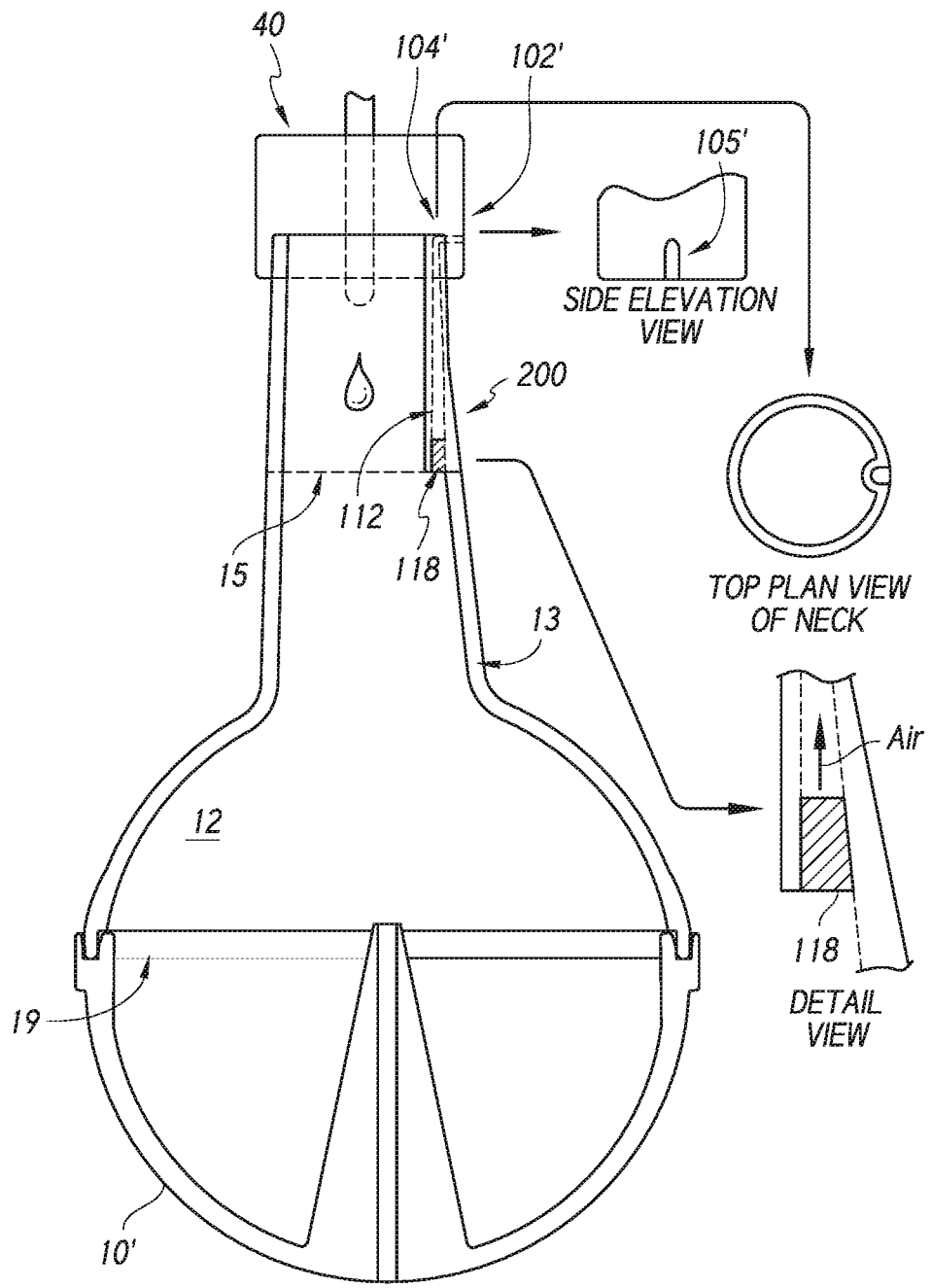
FIG. 3 show a simplified illustration of a drip chamber with an integrated auto vent-shutoff feature according to further examples herein.

In yet other embodiments, the vent pickup tube 110 may be integrated into the wall of the drip chamber 100, for example in the substantially cylindrical wall of the neck portion. Referring now to FIG. 3, another embodiment of an autovent assembly is shown and described. FIG. 3 shows a drip chamber 10' and a cap 40. Similar to drip chamber 10, the drip chamber 10' is configured as an emboli-reducing drip chamber and has a substantially spherical body and substantially cylindrical neck portion 13. The neck portion 13 includes an autovent 200 having a passage 112 integrally formed with the wall of the neck portion 13 and a plug 118 within the passage 112. The autovent may include a single passage as shown in FIG. 3, or multiple passages at different radial locations of the neck portion 13. The cap 40 includes a vent 102' which has a vent opening 104' configured to align with the distal opening of the autovent 200. The vent 102' is open to ambient air through an opening 105', shown here on the peripheral wall of the cap 40 but which may be located elsewhere. Alignment features may be provide at the mating interface between the neck portion 13 and the cap 40, respectively to ensure that the vent 102' in the cap 40 aligns with the autovent 200 (e.g., the distal opening of passage 112) in the drip chamber during assembly thereof.

Figure 4:
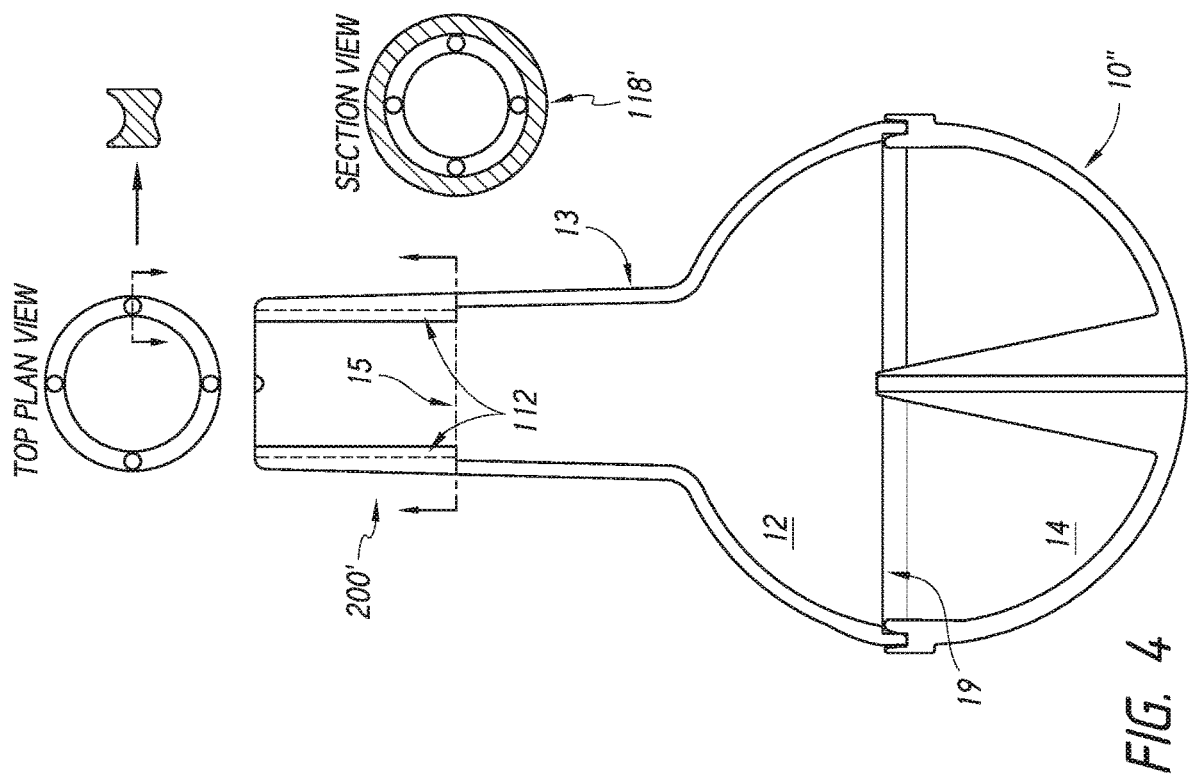
FIG. 4 shows another simplified illustration of a drip chamber with an integrated auto vent-shutoff feature according to further examples herein.

In another embodiment of drip chamber 10" shown in FIG. 4, the autovent 200' is implemented by a plurality of passages 112 formed integrally with the drip chamber 10", at different radial location around the cylindrical neck portion 13. Any suitable number of passages 112 (e.g., 2 at opposite radial locations, 3 passage radially distributed, 4 passages equally radially spaced, etc.) may be used. Individual filter plugs may be placed in each of the passages (e.g., near the proximal or interior opening of each passage 112) to substantially block the outflow of liquid through a passage 112 while permitting air to vent out of the passage 112 as the drip chamber is being filled up to its fill line (e.g., at line 15 or wherever vertical location of the filter plugs is selected). In another implementation, the proximal opening of the autovent 200' may be implemented as an annular channel formed in a ledge projection from the inner wall of the neck portion 113. The annular channel may communicate air, e.g., through one or a plurality (e.g., 2, 3, 4, 5, or more) of passages 112 to the distal end of the neck portion (e.g., to the rim of the neck). In this implementation, the filter plug 118' may be implemented as an annular ring that sits within the annular channel that serves as the proximal opening. For manufacturability the upper and lower portions 12 and 14, respectively, of an emboli-reducing drip chamber (e.g., drip chamber 10, 10', 10") may be manufactures as separate components and joined at a seam 11. This may facilitate the integration of the autovent feature in the neck portion.

Figure 5:
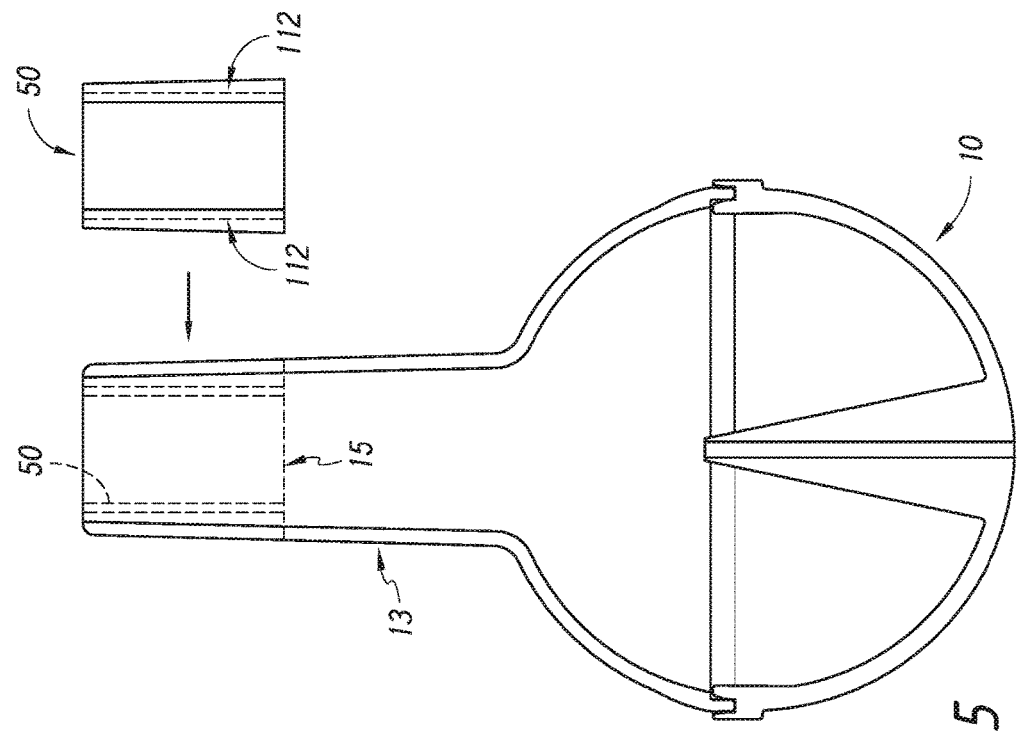
FIG. 5 shows a simplified illustration of a drip chamber and neck insert with an integrated auto vent-shutoff feature according to examples of the present disclosure.

In yet other examples, the autovent may be integrated into a neck insert 50 formed separately from the drip chamber 10, as shown in FIG. 5. The neck insert 50 may be used to retrofit any non-self-regulated drip chamber with an autovent feature as described herein. For example the neck insert 50 may be configured to be used with drip chamber 10 in place of the autovent assembly 100 that is configured to couple to the cap. A neck insert 50 may be substantially corresponding in shape to the upper part of the neck 13 of the drip chamber 10. The neck insert 50 may be manufactured separately from the body of the drip chamber 10 and may make the integration of the autovent feature easier than incorporating it into the drip chamber body. In some examples, e.g., for a substantially cylindrical or a frustoconical neck, the neck insert 50 may be implemented by a corresponding cylindrical or frustoconical, substantially hollow or tubular body. The outer surface profile (e.g., outer diameter(s)) of the neck insert 50 may be sized for a tight fit (e.g., an interference fit) with the upper portion of the neck 13. The one or more passages 112 are formed within the thickness of the neck insert 50 such that they are substantially fully enclosed within the neck insert's wall. The vertical dimension or height of the neck insert 50 may be determined based on the desired vertical location of the fill level within the neck 13. For example, in embodiments in which the proximal opening(s) of the autovent are located at the bottom rim of the neck insert 50 and the distal opening(s) of the autovent may be located at the top rim thereof. One or more aquaphobic filter plugs are provided across the proximal opening(s), the distal opening(s), or both, and/or optionally inserted into the passages 112 to block the liquids from passing through the passage 112. When assembled or retrofitted to a drip chamber 10, the neck insert 50 may be frictionally retained within the neck 13. In some embodiments, the neck insert may additionally or alternatively be bonded within the neck 13. In the illustrated example, the bottom edge of the neck insert 50 sets the fill level 15. The vent openings) of the autovent are thus placed within the drip chamber 10, spaced from the upper or distal enclosing structure of the drip chamber, namely the cap (not shown in FIG. 5), to define and maintain an air pocket of a desired size. The examples of autovents shown in FIGS. 3-5 may provide an effectively single part solution to the autovent assembly in FIG. 1 by, in effect, integrating the pickup tube into the wall of the drip chamber. The examples in FIGS. 3-5 may be well suited for a traditional, vertical orientation, gravity fed IV system since tilting of the drip chamber from its vertical orientation may disturb the fluid seal provided by the autovent feature and permit the inadvertent additional venting of air. Once the drip chamber is stably positioned on its side the air pocket may have transferred within and near the wall of the spherical portion and the vent openings may remain submerged in fluid and sealed through use. A fewer number of passages 112 (e.g., a single vent passage) may be used to reduce the risk of temporarily disrupting the autovent seal when tilting the drip chamber.

Returning back to the example in FIG. 1, with an all position drip chamber which is designed to operate properly irrespective of its orientation, the likelihood that the drip chamber would be tilted from vertical is greater and thus there is a chance that the autovent shut off or seal provided by the fluid effectively plugging the fluid passage of the pickup tube is temporarily disturbed. To reduce this risk, the autovent structure that includes the pickup tube may be configured to place the pickup tube, or at least its proximal opening as close to the centerline of the drip chamber as practical without interfering with the flow (during priming) or dripping (during use) of the fluid into the drip chamber. Therefore, the pickup tube 110 is configured to be offset as far inwardly from the walls of the neck portion 13 as practical without the pickup tube coming into the path of the fluid passage 23. In some embodiments, a plurality (e.g., two or more) of pickup tubes 110 may be suspended from the ring base 119 at different radial location of the ring base 119. The passages 112 of the tubes 110 may be fluidly connected via an annular passage 113 in the ring base 119 such that any liquid entering through any of the passages 112 is communicated to the annular passage 113 in the ring base. The aquaphobic plug 118 may be provided upstream of the annular passage 113 such that any liquid communicated into the annular passage 113 via one or more of the passage 112 is substantially blocked from flowing into the vent 102. Providing multiple pickup tubes 110 in this manner may ensure that at least one proximal opening remains submerged in fluid, even if the drip chambers is tilted or jostled around exposing one or more of the proximal openings to the air pocket, which in turn ensures that liquid fills the passage 113 and blocks outflow of the liquid through the vent 102 thereby reducing the inadvertently breaking of the "seal" of the autovent during rough handling of the drip chamber.

In the preceding examples, the air vent is located generally at the top of the drip chamber, and thus the pickup tubes of the autovent feature extend proximally or downstream to place the air vent intake at the desired fill level. In other examples, the air may be vented out of the drip chamber at a different location around its periphery. For example, the air vent, and thus the vent opening, may be located at the proximal side of the drip chamber (e.g., near the outlet of the drip chamber). In such embodiments, the pickup tube(s) of the autovent may extend distally or upstream to place the air vent intake internally and at the desired fill level 225 to set the size of the air pocket 226. FIGS. 6A and 6B show one such example, in which the air vent 202 of the drip chamber 208 exhausts at the proximal side 204 thereof, e.g., near the outlet 206 of the drip chamber 208. The air vent 202 may include one or more through openings formed in the body of the drip chamber 208 to communicate the air out of the drip chamber. The pickup tube 210 of the autovent feature extends from the proximal side 204 inwardly toward the distal side 218 thereof, placing the air vent intake 216 within the interior (or interior volume) 214 of the drip chamber 208. The pickup tube 210 may define one or more passages 212 that communicate air from the interior 214 of the drip chamber 208, via the air vent intake 216, to the air vent 202 and thus to the exterior (or ambient air) 213. To reject (i.e. substantially prevent any) liquid from flowing out of the air vent, a filter plug 224 is operatively associated with the pickup tube 210. In this example, the filter plug 224, which may be provided by a GVS 1-2 micron filter, as an example, or any other suitable filter, is located at the distal end of the pickup tube 210, near the slits (or through-openings) 222 that form the air vent intake 216. Placing the filter plug near the air vent intake ensures that liquids (e.g., the IV fluid) is substantially prevent from passing into the pickup tube 210, while air can be vented out when the level of the liquid (e.g., IV fluid) in the drip chamber falls below the fill level 225. As such the autovent functions to automatically set the size of the air pocket 226, e.g., during priming of the drip chamber, and to automatically control or regulated the air pocket's size to the desired size during use of the drip chamber. By having a means, as described herein to automatically set and regulate the size of the air pocket 226 in the drip chamber, the need for increased care by the user and/or the risk associated with user error when priming and operating the infusion system is reduced because the size of the air pocket is regulated or managed in a manner outside of the user's control. For example, during priming, particularly with a rapidly priming system like the priming apparatus 30 of FIG. 1, the autovent of the present disclosure prevents too much air from venting out by automatically shutting off, by virtue of the air vent intake becoming submerged in the liquid, when the liquid reaches the internally-projecting air vent intake, placed at the desired fill level. During infusion, the air vent automatically opens when the fluid in the drip chamber drops below the desired fill level and air vents out of the drip chamber. The air venting out may create a temporary drop in air pressure in the drip chamber which in turn draws fluid out of the IV bag and into the drip chamber to maintain the size of the air pocket to the regulated size. As such, the autovent not only sets and prevents the fluid level in the drip chamber from rising above the desired fill line but may also facilitate the introduction of additional fluid in the drip chamber when the fluid level drops below the desired fill line. The filter plug may be operatively associated with the pickup tube so as to be above the fill level when the drip chamber is vertically oriented, thereby setting the desired fill level. The filter plug may be placed in relation to the air vent intake (either above, in the case of downwardly projecting pickup tube, or below, in the case of upwardly projecting pickup tube) such that the air vent intake and plug are on opposite sides of the fill line.

Referring back to the example in FIG. 6, the pickup tube 210 extends substantially along the centerline of the drip chamber 208, with its proximal end branching off and around the centrally located outlet 206 tube of the drip chamber 208. As such, the air vent intake 216 is positioned substantially in the center of the cross-section at the fill level 225, which can ensure that the air vent intake remains submerged in fluid when the drip chamber is filled to the fill line 225 irrespective of the orientation of the drip chamber 208, reducing the risk of disruption of the operation of the auto shutoff feature of the autovent.

Figure 7:
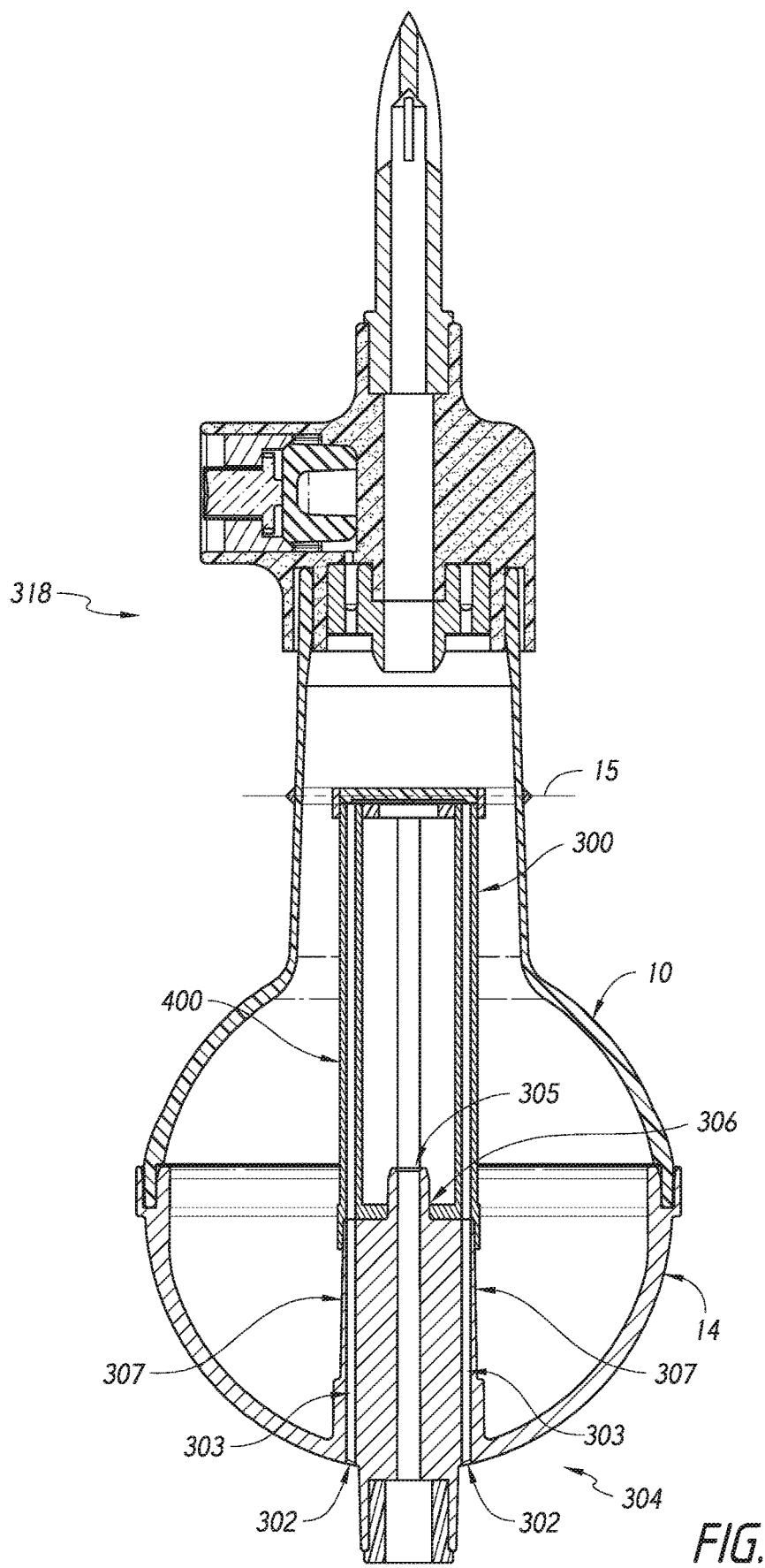
FIG. 7 shows an isometric view of a drip chamber with a portion thereof cutaway to show an auto vent assembly according to further examples herein within the interior of the drip chamber.

FIG. 7 shows another example of an autovent assembly 300, shown here in use with drip chamber 10. The drip chamber 10 is an all position drip chamber which has an outlet 305 positioned generally centrally within the substantially spherical lower portion of the drip chamber 10 to ensure that the outlet 305 remains submerged in the liquid irrespective of the orientation of the drip chamber as long as the drip chamber is filled to a predetermined level (e.g., fill level 15). The outlet 305 is provided at the distal end of an outlet tube 306, which is supported by lateral supports 307. Two, three, four or more lateral supports 307 may be arranged radially around tube 306 to support it at its inwardly extended position. In preferred embodiments, the centrally projecting outlet structure 309 that includes the lateral supports 307 and outlet tube 306 is integrally formed, as a monolithic body, with the lower portion 14 of the drip chamber 10, via any suitable manufacturing process, such as injection molding, machining, 3D printing or other.

One or more vent openings 302 of the autovent assembly 300 are provided in the proximal side 304 of the drip chamber 10, each connected to the interior of the drip chamber 10 via a respective vent passage 303 within a respective lateral support 307. In this example, four vent passages 303 are formed, each extending through one of four lateral supports 307, but in other examples fewer or greater number of vent openings and respective vent passage may be used. A cage 400 is operatively coupled to the vent opening(s) 302.

Figure 8A:
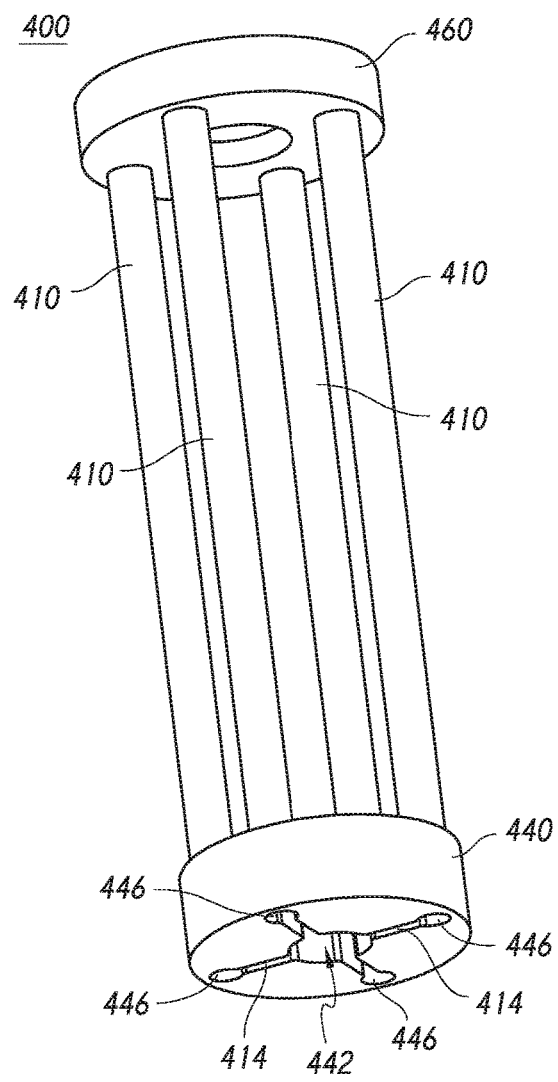
FIGS. 8A-8C show an isometric view, a cutaway isometric view, and an enlarged partial view of the cutaway isometric view, respectively, of the air vent intake cage of the auto vent assembly in FIG. 7.
Figure 8B:
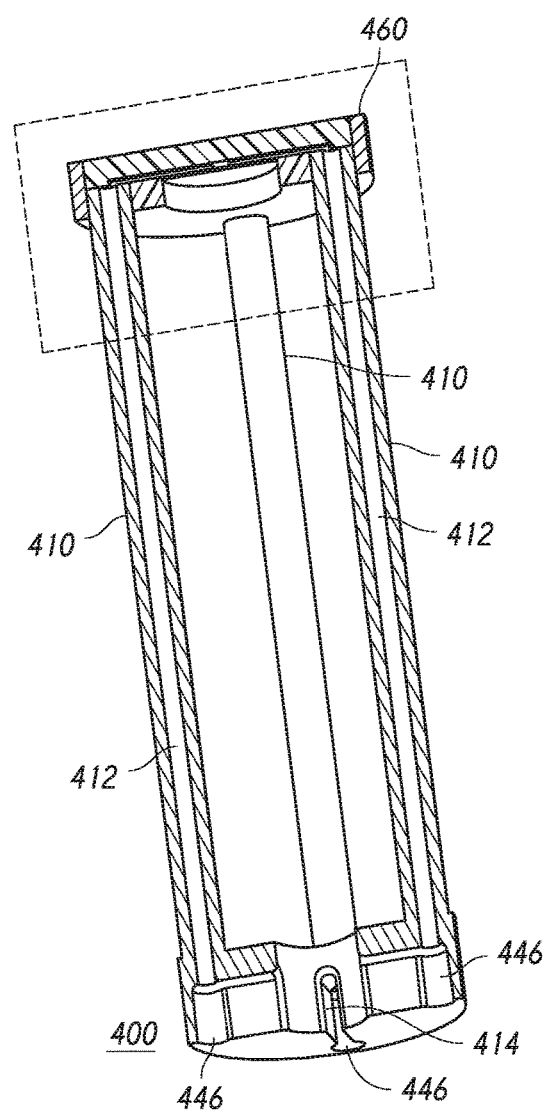
Figure 8C:
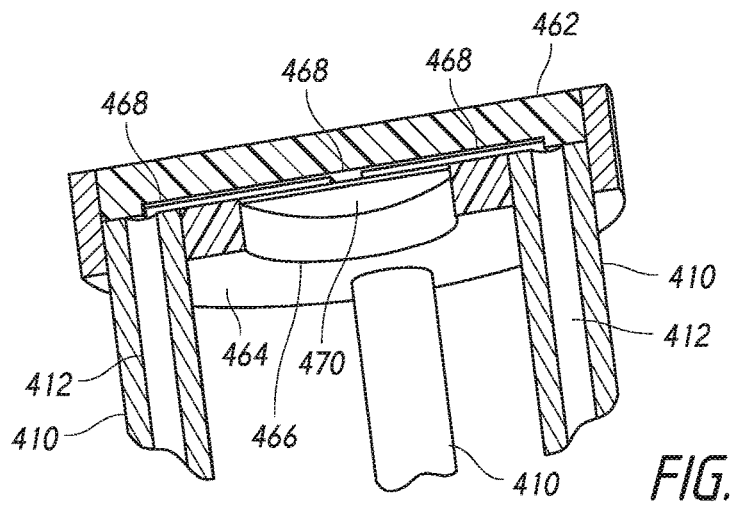

The cage 400, which is shown in isolation in FIGS. 8A-8C, includes a plurality of pickup tubes 410 extending from a base 440 to a roof 460 of the cage 400. Each of the pickup tubes 410 defines an enclosed fluid passage 412 that runs the length of the tube 410. The base 440 is configured to fit over the structure 309, with the outlet 305 exposed to the drip chamber's interior. The base includes central through-opening 442 that receives the outlet tube 306, and slots 414 corresponding in number to the lateral supports 307 to receive a respective lateral support 304. The slots 414 extend radially from the central through-opening 442 to peripheral through-openings 446 which align with the vent passages in the pickup tubes 410. The roof 460 of the cage 400 includes an upper plate 462 and a lower plate 464. The lower plate 464 includes a center hole 466 extending through the thickness of the plate 464. The upper plate 462 has a plurality of interconnected grooves 468 formed on the inner side of the plate 462 that faces the lower plate 464. As such, the grooves 468 with the facing side of plate 464 form enclosed fluidic passages that communicate air from the center hole 466 to the periphery of the upper plate 462. The pickup tubes 410 are connected to the periphery of the roof 460 such that the fluid passage 412 of each pickup tube 410 is in communication with the network of interconnected grooves 468. For example, in the case of a cage having four pickup tubes which are equally radially distributed around the periphery of the cage, the interconnected network of grooves 468 may be formed in a cross pattern, with the fluid passage of each of the four pickup tubes connected to one of the four ends of the cross pattern. The filter plug, in this example, may be provided by a filter layer 470 sandwiched between the upper and lower plates 462 and 464, respectively, such that the fluid path from the interior of the drip chamber 10 first passes through the filter layer 470 before entering the fluid passages 412 of the pickup tubes 410. This arrangement prevents liquid from passing into the air vent (e.g., into the fluid passages 412), while allowing air to vent out of the air vent (e.g., through the fluid passages 412) when the liquid level is below the level of the filter layer 470. As described, an autovent according to the present examples can automatically set and protect the size of the air pocket, and may optionally assist with maintaining the fluid level. The benefits provided by an autovent according to any of the examples herein may be applicable to and can be used with a drip chamber of any drip chamber configuration, whether equipped with a priming apparatus or not, whether configured to reduce embolism risk or not, and/or whether used in pressure-assisted infusion or under conventional gravity infusion.

This description of examples is provided to aid in understanding of the present disclosure. Each of the various aspects and features of the disclosure may advantageously be used separately in some instances, or in combination with other aspects and features of the disclosure in other instances. Accordingly, while the disclosure is presented in terms of examples, individual aspects of any example can be claimed separately or in combination with aspects and features of that example or any other example. This description of examples is neither intended nor should it be construed as being representative of the full extent and scope of the present disclosure. The present disclosure is set forth in various levels of detail in this application and no limitation as to the scope of the claimed subject matter is intended by either the inclusion or non-inclusion of elements, components, or the like in this description. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A drip chamber for intravenous (IV) fluid infusion, the drip chamber comprising:
    a drip chamber body having a proximal region and a distal region each at least partially defining an internal volume within an interior of the drip chamber body;
    an inlet tube configured to drip the IV fluid into the interior of the drip chamber at the distal region;
    an outlet tube extending inward into the interior of the drip chamber body from the proximal region, the outlet tube being in fluid communication with the interior of the drip chamber body to allow the IV fluid to flow out of the drip chamber body; and
    a vent configured to automatically set and maintain an air pocket of predetermined size within the interior of the drip chamber, wherein the vent comprises a vent opening at the proximal region coupling the interior of the drip chamber to ambient air, and a pickup tube extending inward into the interior of the drip chamber body from the proximal region, the pickup tube having a first end disposed in the proximal region and in fluid communication with the vent opening, and a second end comprising an air vent intake at a location in the distal region that is spaced apart from the vent opening to define the predetermined size of the air pocket.

2. The drip chamber of claim 1, wherein the vent comprises an aquaphobic filter operatively coupled to the second end of the pickup tube near the air vent intake, the aquaphobic filter configured to substantially prevent the IV fluid from passing therethrough.

3. The drip chamber of claim 1, wherein the pickup tube extends into the interior of the drip chamber to a location located distally from an internal opening of the outlet tube.

4. The drip chamber of claim 1, wherein the pickup tube is spaced apart from a wall of the drip chamber.

5. The drip chamber of claim 1, wherein the air vent intake is substantially axially aligned with a distal opening of the outlet tube.

6. The drip chamber of claim 1, wherein the pickup tube is one of a plurality of pickup tubes of a vent cage positioned above and co-axially aligned with the outlet tube, each of the plurality of pickup tubes arranged radially around a periphery of the vent cage.

7. The drip chamber of claim 6, wherein the vent opening is provided by a plurality of discrete through-holes in a proximal wall of the drip chamber, the plurality of discrete through-holes corresponding in number to the plurality of pickup tubes, and wherein the vent cages comprises:
    a base configured to provide each of the plurality of pickup tubes in fluid communication with a corresponding one of the plurality of discrete through-holes;
    a roof that defines a central blind hole substantially coaxial with and facing the outlet tube, wherein the air vent intake opening of each of the plurality of pickup tubes is in fluid communication with the central blind hole; and
    an aquaphobic filter across the central blind hole such that a fluid path from the interior of the drip chamber to each of the plurality of pickup tubes passes through the aquaphobic filter.

8. The drip chamber of claim 1, wherein the drip chamber body includes a generally cylindrical portion disposed at the distal region and a generally spherical portion disposed at least partially at the proximal region.

9. The drip chamber of claim 8, wherein the air vent intake is disposed in the generally cylindrical portion and the pickup tube extends distally into the internal volume from the vent opening through the generally spherical portion and at least partially into the cylindrical portion.

10. A drip chamber for intravenous (IV) fluid infusion, the drip chamber comprising:
    a drip chamber body having a proximal region and a distal region each at least partially defining an internal volume within an interior of the drip chamber;
    an inlet tube configured to drip the IV fluid into the interior of the drip chamber at the distal region;
    an outlet tube extending inward into the interior of the drip chamber body from the proximal region, the outlet tube being in fluid communication with the interior of the drip chamber to allow the IV fluid to flow out of the drip chamber; and
    an air vent configured to automatically prevent venting of gases out of the interior of the drip chamber if the IV fluid filling the interior of the drip chamber is above a predetermined fill level, and to automatically vent gases out of the drip chamber when the IV fluid falls below the predetermined fill level, the predetermined fill level corresponding to a volume less than the internal volume of the drip chamber, wherein the air vent includes an exhaust disposed at the proximal region, an air vent intake disposed in the internal volume, and a pickup tube extending distally into the internal volume from the exhaust towards the air vent intake to fluidly couple the air vent intake and the exhaust.

11. The drip chamber of claim 10, further comprising an aquaphobic filter disposed proximate to the air vent intake, the aquaphobic filter configured to substantially prevent the IV fluid from passing therethrough into the pickup tube.

12. The drip chamber of claim 10, wherein the drip chamber body includes a generally cylindrical portion disposed at the distal region and a generally spherical portion disposed at least partially at the proximal region.

13. The drip chamber of claim 12, wherein the air vent intake is disposed in the generally cylindrical portion and the pickup tube extends distally into the internal volume from the exhaust through the generally spherical portion and at least partially into the cylindrical portion.

14. The drip chamber of claim 10, wherein the pickup tube is spaced apart from a wall of the drip chamber.

15. The drip chamber of claim 10, wherein the pickup tube extends substantially along a longitudinal center axis of the drip chamber.

16. The drip chamber of claim 10, wherein the air vent intake is substantially axially aligned with a distal opening of the outlet tube.

17. The drip chamber of claim 10, wherein the pickup tube is one of a plurality of pickup tubes of a vent cage positioned above and co-axially aligned with the outlet tube, each of the plurality of pickup tubes arranged radially around a periphery of the vent cage.

18. The drip chamber of claim 10, further comprising a cap covering the air vent intake.

19. The drip chamber of claim 18, wherein the cap comprises a substantially triangular profile.

* * * * *